US012256976B2

(12) United States Patent
McLawhorn

(10) Patent No.: US 12,256,976 B2
(45) Date of Patent: Mar. 25, 2025

(54) ELECTROSURGICAL SYSTEM WITH ELECTRICALLY ACTIVE OUTER SURFACE

(71) Applicant: Cook Medical Technologies LLC, Bloomington, IN (US)

(72) Inventor: Tyler E. McLawhorn, Winston-Salem, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 697 days.

(21) Appl. No.: 17/493,433

(22) Filed: Oct. 4, 2021

(65) Prior Publication Data

US 2022/0022938 A1     Jan. 27, 2022

Related U.S. Application Data

(62) Division of application No. 14/209,422, filed on Mar. 13, 2014, now abandoned.
(Continued)

(51) Int. Cl.
    *A61B 18/14*      (2006.01)
    *A61B 1/00*      (2006.01)
    (Continued)

(52) U.S. Cl.
    CPC .......... *A61B 18/14* (2013.01); *A61B 1/00087* (2013.01); *A61B 1/00114* (2013.01); *A61B 1/018* (2013.01); *A61B 18/1492* (2013.01); *A61B 2018/00482* (2013.01); *A61B 2018/00494* (2013.01); *A61B 2018/00553* (2013.01);
(Continued)

(58) Field of Classification Search
    CPC ..... A61B 18/14; A61B 18/1492; A61B 1/018; A61B 2018/00553; A61B 2018/00982; A61B 2018/1425; A61B 2018/144; A61B 2018/1475; A61B 2018/00494; A61B 2018/00482
See application file for complete search history.

(56) References Cited

U.S. PATENT DOCUMENTS 4,823,791 A    4/1989   D'Amelio
4,979,496 A    12/1990   Komi
(Continued)

FOREIGN PATENT DOCUMENTS

WO    WO 1997/024074      7/1997

OTHER PUBLICATIONS

United States Statutory Invention Registration No. H1745, Published Aug. 4, 1998, Inventor Joseph F. Paraschac.
(Continued)

*Primary Examiner* — Thomas A Giuliani
*Assistant Examiner* — Abigail M Ziegler
(74) *Attorney, Agent, or Firm* — Crowell & Moring LLP

(57) ABSTRACT

An electrosurgical system may include a medical delivery device and an electrosurgical device to perform an electrosurgical procedure. The electrosurgical device may have a monopolar configuration. An outer surface of the medical delivery device may include a conductive portion that is part of a return path for a bipolar configuration. Current may be supplied through an active member of the electrosurgical device to perform the procedure. After passing through tissue, the current may be drawn to the electrode portion of the medical delivery device to complete the circuit.

9 Claims, 10 Drawing Sheets

Related U.S. Application Data

(60) Provisional application No. 61/798,262, filed on Mar. 15, 2013.

(51) Int. Cl.
  *A61B 1/018* (2006.01)
  *A61B 18/00* (2006.01)

(52) U.S. Cl.
  CPC ............... *A61B 2018/00982* (2013.01); *A61B 2018/1425* (2013.01); *A61B 2018/144* (2013.01); *A61B 2018/1475* (2013.01)

(56) References Cited

U.S. PATENT DOCUMENTS

| | | | |
|---|---|---|---|
| 5,007,908 | A | 4/1991 | Rydell |
| 5,035,696 | A | 7/1991 | Rydell |
| 5,201,732 | A | 4/1993 | Parins et al. |
| 5,330,471 | A | 7/1994 | Eggers |
| 5,417,687 | A | 5/1995 | Nardella |
| 5,462,545 | A | 10/1995 | Wang |
| 5,573,534 | A | 11/1996 | Stone |
| 5,814,044 | A | 9/1998 | Hooven |
| 5,941,817 | A | 8/1999 | Crawford |
| 6,022,313 | A | 2/2000 | Ginn |
| 6,113,594 | A | 9/2000 | Savage |
| 6,322,494 | B1 | 11/2001 | Bullivant et al. |
| 6,328,734 | B1 | 12/2001 | Zappala |
| 6,394,949 | B1 | 5/2002 | Crowley |
| 6,497,706 | B1 | 12/2002 | Burbank et al. |
| 6,517,530 | B1 | 2/2003 | Kleven |
| 6,610,059 | B1 | 8/2003 | West, Jr. |
| 6,730,081 | B1 | 5/2004 | Desai |
| 6,837,884 | B2 | 1/2005 | Woloszko |
| 6,855,145 | B2 | 2/2005 | Ciarrocca |
| 7,182,763 | B2 | 2/2007 | Nardella |
| 7,232,439 | B2 | 6/2007 | Ciarrocca |
| 7,879,034 | B2 | 2/2011 | Woloszko et al. |
| 2001/0014804 | A1 | 8/2001 | Goble |
| 2001/0020167 | A1 | 9/2001 | Woloszko |
| 2003/0014051 | A1 | 1/2003 | Woloszko |
| 2003/0176880 | A1 | 9/2003 | Long |
| 2003/0181905 | A1 | 9/2003 | Long |
| 2004/0181219 | A1 | 9/2004 | Goble |
| 2006/0069303 | A1 | 3/2006 | Couvillon |
| 2007/0066870 | A1 | 3/2007 | Ohashi |
| 2007/0142709 | A1 | 6/2007 | Marton |
| 2008/0255441 | A1 | 10/2008 | Hadani |
| 2009/0043303 | A1 | 2/2009 | Shimomura |
| 2009/0048592 | A1 | 2/2009 | Thomas |
| 2010/0211076 | A1 | 8/2010 | Germain |
| 2010/0228202 | A1 | 9/2010 | O'Dea |
| 2010/0312240 | A1 | 12/2010 | Boulnois et al. |
| 2010/0324363 | A1 | 12/2010 | Solanki |
| 2011/0190596 | A1 | 8/2011 | Hacker |
| 2012/0016190 | A1* | 1/2012 | Yanuma ............ A61B 18/1492 600/104 |
| 2012/0059286 | A1 | 3/2012 | Hastings |
| 2012/0059373 | A1* | 3/2012 | Suzuki ............ A61B 18/1492 606/41 |
| 2012/0239033 | A1 | 9/2012 | Van Wyk et al. |
| 2013/0046138 | A1 | 2/2013 | McLawhorn |
| 2013/0046300 | A1 | 2/2013 | Binmoeller |
| 2013/0172870 | A1 | 7/2013 | Germain |
| 2014/0031834 | A1 | 1/2014 | Germain |
| 2014/0100570 | A1 | 4/2014 | McLawhorn |
| 2014/0188109 | A1 | 7/2014 | McLawhorn |
| 2015/0133924 | A1 | 5/2015 | McLawhorn |
| 2016/0089199 | A1 | 3/2016 | Sartor |

OTHER PUBLICATIONS

Wataru Makishi et al, "Active Bending Electric Endoscope Using Shape Memory Alloy Coil Actuators", Jun. 6, 2001, 3 pages.

International Search Report and Written Opinion for corresponding application No. PCT/US2014/020612 mailed May 26, 2014.

Sulochana, S., et al. "Gross Morphology of Major and Minor Duodenal Papilla: a Cadaveric Study." National Journal of Clinical Anatomy, vol. 02, No. 02, 2013, pp. 061-066., doi:10.1055/s-0039-3401708. (Year: 2013).

Crelin, Edmund S. Functional Anatomy of the Newborn. Yale University, 1973. p. 57.

* cited by examiner

ELECTROSURGICAL SYSTEM WITH ELECTRICALLY ACTIVE OUTER SURFACE

CROSS REFERENCE TO RELATED APPLICATION

This application is a divisional of U.S. Non-Provisional application Ser. No. 14/209,422, filed Mar. 13, 2014, which claims the benefit of U.S. Provisional Application No. 61/798,262, filed Mar. 15, 2013. The contents of U.S. Non-Provisional Application No. 14/209,422 and U.S. Provisional Application No. 61/798,262 are incorporated by reference in their entirety.

TECHNICAL FIELD

The present invention relates generally to medical devices, and more particularly to electrosurgical medical devices and systems.

BACKGROUND

Electrosurgery may include the application of high frequency electrical current to biological tissue at a treatment to perform an operation on the tissue, such as cut or coagulation. Endoscopes may be used to provide visualization of the treatment site to an operator or physician performing the electrosurgery. The endoscope may include a lumen or channel that is sized for advancement of an electrosurgical device to perform the electrosurgical procedure.

BRIEF SUMMARY

The present description describes systems, devices, and methods to perform electrosurgical procedures. In a first aspect, a bipolar electrosurgical system configured to perform an electrosurgical procedure at a treatment site within a patient may include an electrosurgical device; and a medical delivery device configured to deliver a distal end of the electrosurgical device to the treatment site. The electrosurgical device may include an active member that is configured as part of an active path for the bipolar electrosurgical system. In addition, the medical delivery device may include a conductive portion that is at least one of disposed on or integral with an outer surface of the medical delivery device. The conductive portion may be configured as part of a return path for the bipolar electrosurgical system.

In a second aspect, a method of performing an electrosurgical procedure using a bipolar configuration may include: delivering an outer tubular member of a medical delivery device to a treatment site within a patient. The medical delivery device may include a conductive portion that is at least one of disposed on or integrated with an outer surface of the tubular member the medical delivery device. The medical delivery device may also include a working channel longitudinally extending within the outer tubular member of the medical delivery device. The method may also include contacting a return electrode to a first tissue portion of the patient when a distal portion of the medical delivery device is positioned at the treatment site; and delivering an electrosurgical device within the working channel of the medical delivery device to the treatment site. The electrosurgical device may include an inner tubular member and an active member disposed within the inner tubular member. In addition, the method may include contacting a distal end of the active member of the electrosurgical device with a second tissue portion. Also, the method may include electrically coupling the active member of the electrosurgical device to an active port of a power source; electrically coupling the conductive portion of the medical delivery device to a return port of the power source; and activating the power source to supply electrical current to the treatment site.

In a third aspect, a bipolar electrosurgical system is configured to perform an electrosurgical procedure at a treatment site within a patient. The bipolar electrosurgical system may include an active member electrically coupled to an active port of a power source and an inner tubular member, where the active member movably disposed and longitudinally extending within the inner tubular member. The bipolar electrosurgical system may also include an outer tubular member; and a working channel lumen longitudinally extending within a body of the outer tubular member, where the active tubular member and the inner tubular member are movably disposed within the working channel lumen. The system may also include a conductive portion that is one of disposed on or integrated with an outer surface of the outer tubular member, and where the conductive portion is electrically coupled to a return port of the power source.

In a fourth aspect, an endoscope is configured to operate in a bipolar electrosurgical system. The endoscope may include an elongate tubular member having an outer surface. The endoscope may also include a working channel lumen longitudinally extending within the elongate tubular member. The working channel lumen may be configured to have an electrosurgical device movably disposed within it; and at least one illumination lumen having illumination fibers disposed within it. The illumination fibers may be configured to illuminate a treatment site for visualization using the endoscope. The endoscope may also include a conductive portion that at least one of is disposed on or integral with the outer surface of the elongate tubular member. The conductive portion may be configured for contact with tissue to perform an electrosurgical procedure using a bipolar configuration.

DETAILED DESCRIPTION

Figure 1:
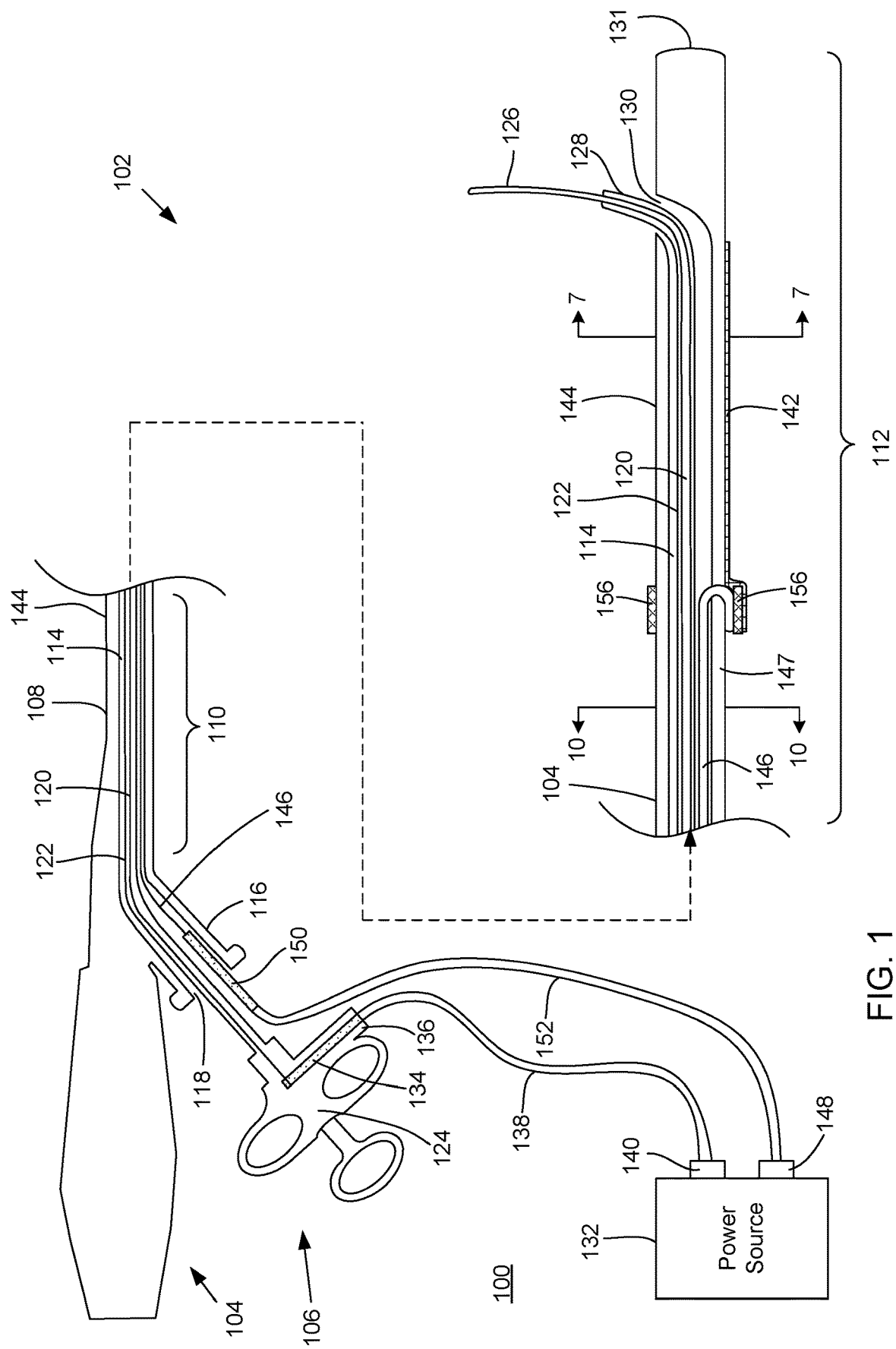
FIG. 1 shows a cross-sectional side view of a medical system that includes a bipolar electrosurgical system.

The present disclosure describes various embodiments of an electrosurgical system that is configured to perform electrosurgical procedures at treatment sites within a patient. The electrosurgical system may include three elongate members—an elongate active member, an elongate inner tubular member, and an elongate outer tubular member. The three elongate members may be parts or components of two different medical devices making up the system. The elongate active member and the elongate inner tubular member may be components of an electrosurgical device that is configured to supply electrical current to the treatment site to perform the electrosurgical procedure. The elongate outer tubular member may be a component of a medical delivery device that is configured to provide a pathway, such as a channel or a lumen, extending from outside of the patient to the treatment site for delivery of the electrosurgical device to the treatment site.

To conduct current to perform an electrosurgical procedure, the electrosurgical system may be used to form an electrical circuit that has an active path and a return path in electrical communication with tissue at the treatment site. The tissue may function as a load due to its resistive properties. The active path, the return path, and the tissue, together may form the electrical circuit, through which the current may be conducted. Typically, the active path and the return path are connected to a power source, such as an electrosurgical unit (ESU), that is configured to supply the electrical current through the circuit. The power source may supply the current through the active path, and the current may be returned back to the power source through the return path.

The electrosurgical system may have a monopolar or a bipolar configuration to perform various electrosurgical procedures. For a monopolar configuration, the active path may include one or more conductive portions of the electrosurgical system extending within the patient to the treatment site and contacting the tissue. The return path may be external to the patient. In particular, the return path may use or include a neutral electrode, which may be a solid, neutral electrode, or a split neutral electrode, and which may be positioned external to the patient undergoing the electrosurgical procedure, such as on the thigh of the patient. The return path, which may include a wire or a cable, may extend external to the patient and have one end connected to the neutral electrode and another end connected to a power source. To perform an electrosurgical procedure with a monopolar configuration, the power source may supply current through the active path to the tissue, where the current then flows to the neutral electrode and through the return path back to the power source.

For a bipolar configuration, the active path may be similar to an active path for a monopolar configuration. However, the return path for a bipolar configuration may differ from a monopolar in that, like the active path, the return path may contact the tissue and include one or more portions of the electrosurgical system extending within the patient. For some configurations, the active path and the return path may extend generally parallel to each other within the patient. To perform an electrosurgical procedure with the bipolar configuration, the power source may supply current through the active path to the tissue, where the current may flow to a return electrode contacting the tissue internal to the patient at the treatment site. The current may then flow through a return path extending within the patient back to the power source.

The electrosurgical system may include an outer surface that has a portion that is conductive. The conductive portion of the outer surface may be configured to be part of either the active path or the return path. For configurations where the conductive portion is part of the return path, the electrosurgical system may have a bipolar configuration. Current may be supplied through the active member contacting the tissue. The current may then flow to the conductive portion of the outer surface, which may also be contacting the tissue and which may be or function as a return electrode for the return path.

For configurations where the conductive portion is part of the active path, the electrosurgical system may have a monopolar configuration. For monopolar configurations, the electrosurgical system may be configured to perform two different electrosurgical procedures, such as a cut procedure and a coagulation procedure, both of which may be performed in a monopolar manner. For the cut procedure, electrical current may be supplied to the active member to cut tissue at the treatment site. The current may then flow outside of the patient to the neutral electrode and back to the power source. During the cut procedure, the active member may be electrically connected to the power source, while the conductive portion may be electrically disconnected from the power source. For the coagulation procedure, electrical current may be supplied through the conductive portion to coagulate tissue at the treatment site. The current may then flow outside of the patient to the neutral electrode. During the coagulation procedure, the conductive portion may be electrically connected to the power source, while the active member may be electrically disconnected from the power source. A switch may be used to switch the electrical connections between the active member and the conductive portion.

The electrical surgical device comprised of the active member and the tubular inner member may be any type of electrosurgical device configured to perform an electrosurgical procedure in a monopolar manner. Example electrosurgical devices may include a sphinctertome, an endoscopic needle knife, or forceps, as examples. Other electrosurgical devices may be included. The active member may be made of a conductive material, such as stainless steel or tungsten, and may be configured to deliver the electrical current to the treatment site. The active member may be disposed within a lumen of the inner tubular member. The inner tubular member, such as a catheter, may be made of an insulating material, such as fluoropolymer materials, including polytetrafluoroethylene (PTFE) or perfluoroalkoxy (PFA), or other materials such as polyethylene, nylon, or fluorinated ethylene, as examples. The combination of the active member and the inner tubular member may form a monopolar configuration in that the return path is not attached to, integrated with, disposed within, or included as part of the inner tubular member. Instead, to perform an electrosurgical procedure using the active member and the inner tubular member, the electrical current may be supplied through the active member, and may be returned using a neutral electrode outside the patient.

Alternatively, when the active and inner tubular members are used with the outer tubular member, the neutral electrode may be excluded and the electrosurgical procedure may be performed in a bipolar manner because the return path may be attached to, integrated with, disposed within, or included as part of the outer tubular member. In this way, while the active member and inner tubular member may be a monopolar electrosurgical device, the electrosurgical system as a whole may be bipolar.

The outer tubular member may be any medical device that may be configured to provide a pathway, such as a channel or a lumen from outside of the patient to the treatment for delivery of the active and inner tubular members (i.e., the monopolar electrosurgical device) to the treatment site. An example outer tubular member may be an endoscope that includes a working or accessory channel configured and/or sized to move an electrosurgical device to and from the treatment site.

FIG. 1 shows a partial cross-sectional side view of a medical system 100 that includes an example electrosurgical system 102 configured to perform one or more electrosurgical procedures. The example electrosurgical system 102 may include an endoscope 104 and an electrosurgical device 106. The endoscope 104 may be a medical device that uses a visualization system, including a light delivery system and a lens system, to capture visual images of a treatment site within a patient. The endoscope 104 may include an elongate tubular member 108 that extends from a proximal portion 110 to a distal portion 112. The tubular member 108 may be considered an outer tubular member of the electrosurgical system 102. The outer tubular member 108 may be inserted into an opening or an incision of the patient and distally moved within the patient until the distal portion 112 is positioned at the treatment site.

The endoscope 104 may include an accessory or working channel 114 that may be configured and/or sized to have the electrosurgical device 106 movably disposed within it. The working channel 114 may longitudinally extend within the tubular member 108 from the proximal portion 110 to the distal portion 112. At or near the proximal portion 110, the endoscope 104 may include a working channel port 116, which may include an opening 118 in communication with the working channel 114.

The electrosurgical device 106 may include an elongate active member 120 disposed within an elongate tubular member 122. The elongate tubular member 122 may be an inner tubular member of the electrosurgical system 102. The combination of the active member 120 and the inner tubular member 122 may be of any monopolar configuration to perform an electrosurgical procedure. As an example, the inner tubular member 122 and the active member 120 may be an endoscopic needle knife, where the active member is a conductive cutting wire movably disposed within a lumen, such as a central lumen, of the inner tubular member 122. Other configurations of the active and inner tubular member 120, 122 are possible. As shown in FIG. 1, the electrosurgical device 106 may include a handle assembly 124 operatively coupled to the active member 120 to move the active member 120 relative to the inner tubular member 122.

Distal ends 126, 128 of the active and inner tubular member 120, 122 may be inserted into the opening 118 of the working channel port 116 and distally moved within the working channel 114 to the distal portion 112, where the active and inner tubular members 120, 122 may extend from the distal portion 112 to the proximal portion 110. At the distal portion 112, the endoscope 104 may include a distal opening 130 in communication with the working channel 114. The distal ends 126, 128 may further be distally advanced to exit the working channel 114 through the distal opening 130, where they may be disposed external the endoscope 104. For some electrosurgical devices 106, outside of the endoscope 104, the distal end 126 of the active member 120 may be moved relative to the distal end 128 of the inner tubular member 122, such as through use of the handle assembly 124, to expose the distal end 126 of the active member 120 for contacting the tissue. For example, the distal end 126 of the active member 120 may be distally advanced past the distal end 128 of the inner tubular member, such as for endoscopic needle knives. As another example, the active member 120 may be retracted to cause a curling motion at the distal ends 126, 128 to extend the distal end 126 of the active member 120 away from the inner tubular member 122, such as for sphincterotomes. Various configurations are possible.

Figure 2:
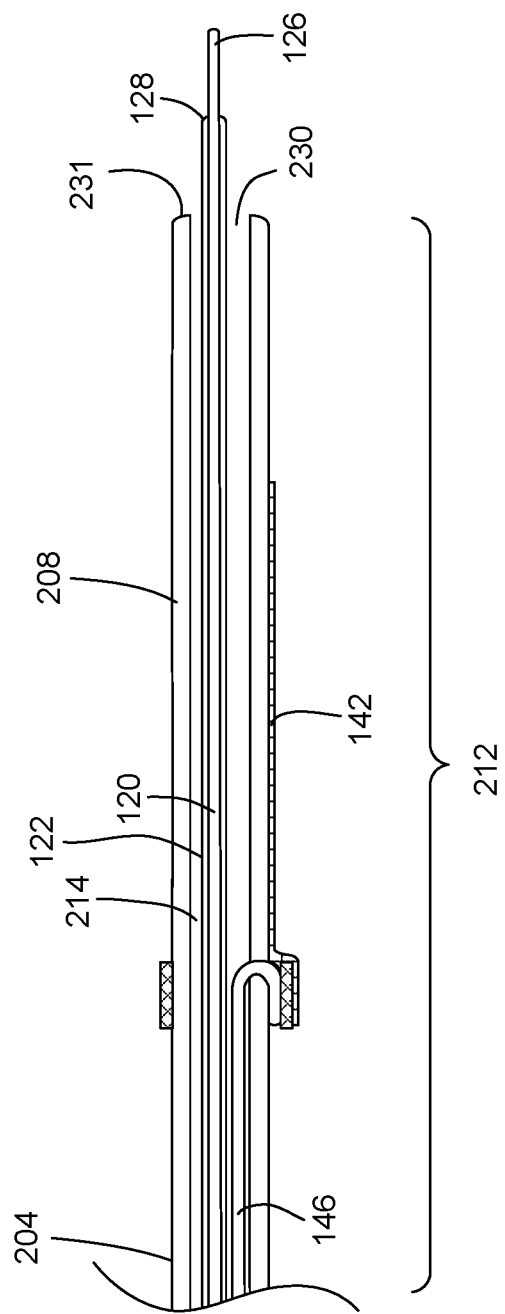
FIG. 2 shows a cross-sectional side view of an alternative embodiment of a distal portion of the bipolar electrosurgical system shown in FIG. 1.

The distal opening 130 shown in FIG. 1 is proximal a distal end 131 of the outer tubular member 108, which may be a configuration for a side viewing endoscope 104. In an alternative configuration, as shown in FIG. 2, the electrosurgical system 102 may include an endoscope 204 with an outer tubular member 208 that has a working channel 214 that, at a distal portion 212, extends to an opening 230 at a distal end 231. Various types of endoscopes may be used, which may depend on the electrosurgical procedure being performed and/or the electrosurgical device 106 being used to perform the electrosurgical procedure.

Referring back to FIG. 1, the active member 120 may be electrically coupled to a power source 132, such as a radio frequency (RF) generator or an electrosurgical unit (ESU), that is configured to supply electrical current to perform the electrosurgical procedure. For some configurations of the electrosurgical device 106, the active member 120 may proximally extend to the handle assembly 124, where a proximal end of the active member 120 may be connected to a conductive pin 134 that extends to a port 136 of the handle assembly 124. The conductive pin 134 and/or the port 136 may be adaptable to connect to supply cabling 138 that may be configured to connect to an active port 140 of the power source 132.

At the distal portion 106, the outer tubular member 108 may have a conductive portion 142 disposed on an outer surface 144 of the outer tubular member 108. The conductive portion 142 may serve or function as a return electrode for the electrosurgical system 102. As a return electrode, the conductive portion 142 may be configured to contact the tissue at the treatment site so that the electrosurgical system 102 may perform an electrosurgical procedure using a bipolar configuration. The conductive portion 142 may be part of a return path that also includes a return wire 146 extending from the distal portion 112 to the proximal portion 110 of the outer tubular member 108.

A length of the conductive portion 142 may vary, depending on the configuration and/or the electrosurgical procedure being performed. The length may be determined to achieve a surface area of the conductive portion 142 that yields or provides a desired current density ratio between the active member 120 and the conductive portion 142. The current density ratio may be at least three-to-one, and a ratio of at least ten-to-one may be optimal. In addition, the conductive portion 142 may be longitudinally disposed along the tubular member 108 at a position that is at or relatively near where the active member 120 is contacting the tissue in order to achieve the benefits of the bipolar configuration, such as reduced heat. For example, the active member 120 and the conductive portion 142 may both contact the tissue at or near the distal portion 112. Conversely, if the conductive portion 142 is at a position along the outer tubular member 108 that is relatively far away from where the active member 120 is contacting the tissue, the configuration between the active member 120 and the conductive portion 142 may behave or function more similarly to a monopolar configuration, and the benefit of the bipolar configuration, such as reduced heat, may be eliminated or reduced.

In some example embodiments, as shown in FIG. 1, the return wire 146 may be disposed and extend within the tubular member 108, from the distal portion 112 to the proximal portion 110. For example, as shown in FIG. 1, the return wire 146 may be disposed and extend within the working channel 114 from the distal portion 112 to the proximal portion 110, such as to the working channel port 116. That is, the return wire 146 may be disposed within the same working channel 114 of the endoscope 104 as the electrosurgical device 106. In alternative configurations, the return wire 146 may be disposed and extend within the tubular member 108 by being disposed in a different channel or lumen other than the working channel, such as a irrigation channel or an air channel (not shown in FIG. 1), as examples. Alternatively, the return wire 146 may be embedded within a body 147 of the outer tubular member 108. Various configurations are possible.

The return wire 146 may be electrically coupled to a return port 148 of the power source 132. For some example configurations, a proximal end of the return wire 146 may be connected to a conductive pin 150, which may be adaptable to connect to return cabling 152 that may to connect to the return port 148.

For configurations where the return wire 146 is disposed within the outer tubular member 108, the conductive portion 142 may be electrically coupled to the return wire 146 in various ways. For example, as shown in FIG. 1, the conductive portion 142 may proximally extend to a conductive ring or cannula 156, which may electrically couple the conductive portion 142 to the return wire 146. In some example embodiments, the conductive cannula 156 may be attached or crimped to the outer surface 144 of the outer tubular member 108. The conductive cannula 156 may be made of metal, such as stainless steel, silver, gold, tantalum, or tungsten, as examples. A part of the conductive portion 142 may be in contact with at least a portion of the conductive cannula 156 so that the conductive portion 142 and the conductive cannula 156 are electrically coupled. To electrically couple the return wire 146 with the conductive cannula 156, the return wire 146 may be curled at its distal end to extend from within the working channel 114 to the outer surface 144 of the tubular member 108. The conductive cannula 156 may be crimped to the tubular member 108 over the distal end of the return wire 148. In an alternative example embodiment, a gap or opening extending from the outer surface 144 to the working channel 114 may include or be filled with a conductive material, such as solder, to connect the distal end of the return wire with the conductive portion. Various configurations are possible.

Figure 3:
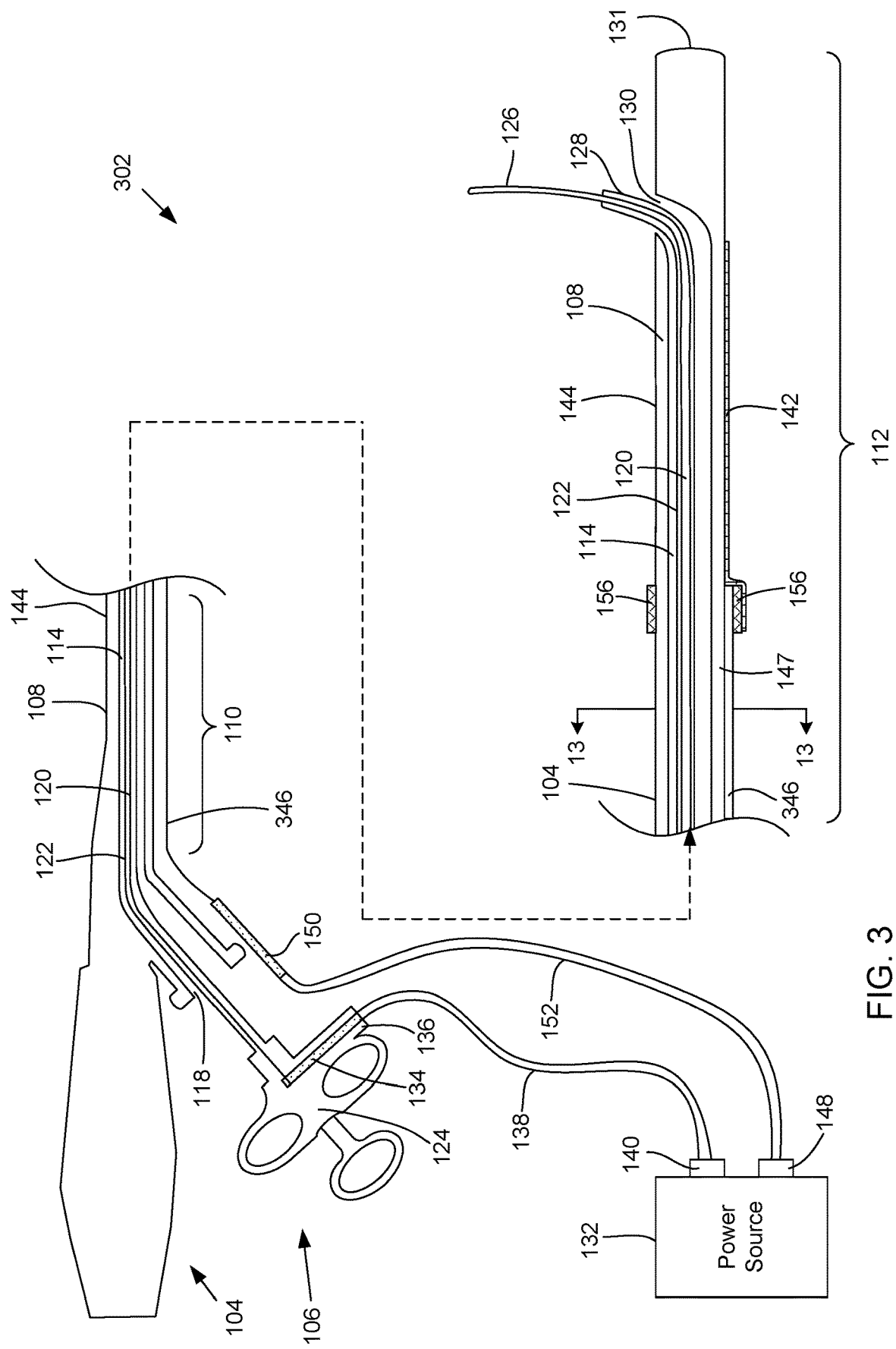
FIG. 3 shows a cross-sectional side view an alternative embodiment of a medical system that includes a bipolar electrosurgical system.

In an alternative example embodiment, as shown in FIG. 3, an electrosurgical system 302 may include a return wire 346 that is disposed external or outside of the tubular member 108. The return wire 346 may extend alongside the outer tubular member 108 from the distal portion 112 to the proximal portion 110, where the return wire 346 may be electrically coupled to the return port 148 of the power source 132, such as by using a conductive pin 150 and return cabling 152, as previously described. At the distal portion 112, the return wire 346 may be electrically coupled to the conductive portion 142 in various ways. For example, the conductive cannula 156 may crimp the return wire 346 to the outer surface 144 of the tubular member 108. In addition or alternatively, the distal end of the return wire 346 may be soldered to the conductive portion 142. For some configurations, the return wire 346 may be attached or adhered to the outer surface 144 of the outer tubular member 108 from the proximal portion 110 to the distal portion 112. Alternatively, the return wire 346 may be unattached to the outer surface 144 of the tubular member 108.

Referring to FIG. 1, 2, or 3, the conductive portion 142 may include various example embodiments and/or may be disposed on the outer surface 144 in various ways. For example, the conductive portion may 142 may include conductive ink that may be applied and/or adhered to the outer surface 144, such as by spraying, pad printing, rolling, brushing, dipping, or electroplating, as examples. Alternatively, the conductive portion 142 may include conductive tape or conductive stickers that may be applied and/or adhered to the outer surface 144. For these example embodiments, the conductive portion 142 may be fixedly attached to the outer surface 144, in that the conductive portion 142 may not be detached from the outer surface 144 without an adhesive remover or scraping operation.

Figure 4:
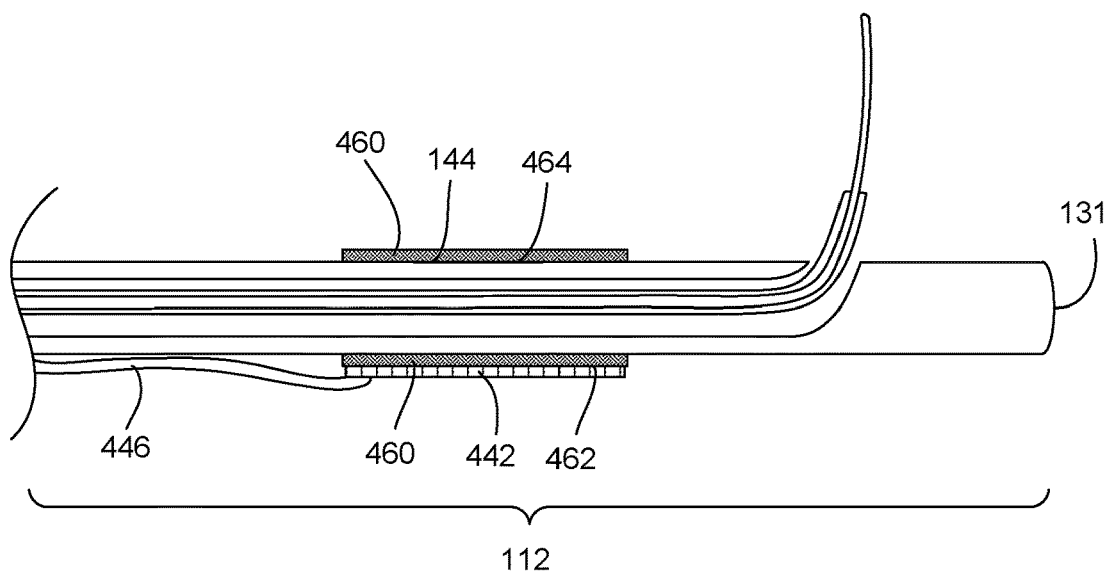
FIG. 4 shows a cross-sectional side view of a sleeve disposed on a distal portion of an outer surface of a medical delivery device.

In alternative example embodiments, the conductive portion 142 may be disposed on the outer surface 144 of the tubular member 108 by being part of a removably attachable electrode that may be disposed about the outer surface 144 of the distal portion 112. An example removably attachable electrode may include a sleeve 460, as shown in FIG. 4. A conductive portion 442 may be disposed on an outer surface 462 of the sleeve 460. The conductive portion 442 may include any of a variety of conductive materials, such as conductive ink, conductive tape, conductive stickers, or plurality of wires, such as a weaved arrangement of wires or a mesh network of wires. Various configurations are possible. An inner surface 464 of the sleeve 460 may form a friction fit with the outer surface 144 of the tubular member 108.

The sleeve 460 may be attached to the outer surface 144 in various ways. For example, the sleeve 460 may be proximally pulled from the distal end 131 by sliding the sleeve 460 over the outer surface 144. Alternatively, the sleeve 460 may include a finger cot or condom-type device that is rolled and expanded over the outer surface 144 to a desired position at the distal portion 112.

As shown in FIG. 4, a return wire 446 may be electrically coupled to the conductive portion 442. For example, the return wire 446 may be soldered to the conductive portion 442, or may be crimped to the conductive portion 442, such as by using the conductive cannula (FIG. 1). Various configurations are possible. From the position where the return wire 446 is coupled to the conductive portion 442, the return wire 446 may proximally extend alongside the outer surface 144 of the endoscope as shown in FIG. 4, or alternatively, may extend to within the outer tubular member 108 as shown in FIG. 1 or 2.

Figure 5:
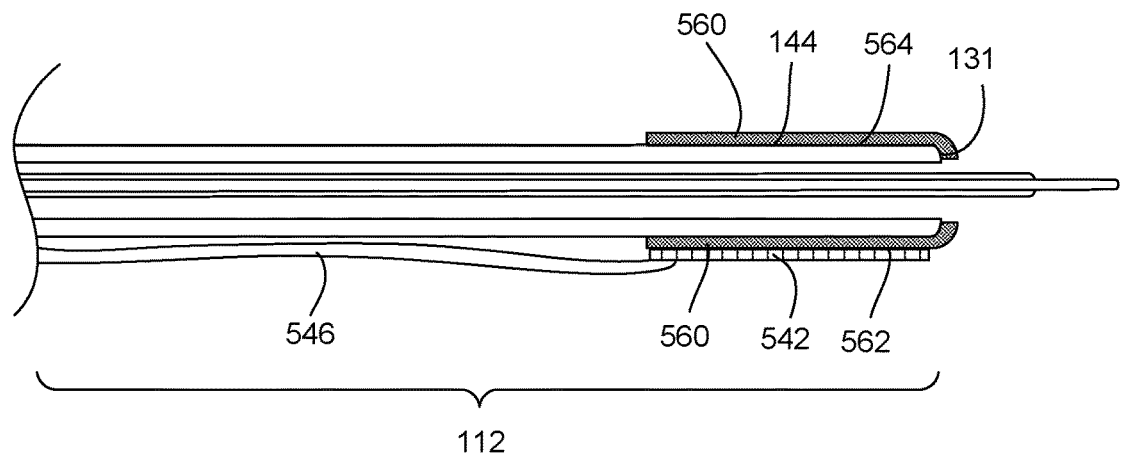
FIG. 5 shows a cross-sectional side view of a cap disposed on a distal portion of an outer surface of a medical delivery device.

An alternative removably attachable electrode may include a cap or an end cap 560, as shown in FIG. 5, that may be disposed about the outer surface 144. Similar to the sleeve 460, a conductive portion 542 may be disposed on an outer surface 562 of the cap 560. An inner surface 564 of the cap 560 may form a friction fit with the outer surface 144 of the tubular member 108. For example, the inner surface 564 may include and/or be coated with a silicone or rubber based material to create friction with the outer surface 144. Also, similar to the sleeve configuration 460, a return wire 546 may be electrically coupled to the conductive portion 542, where the return wire 546 may proximally extend alongside the outer surface 144 as shown in FIG. 5, or alternatively, may extend to within the outer tubular member 108 as shown in FIG. 1 or 2.

The various embodiments of the conductive portion 142 may be used with, integrated with, applied to, and/or disposed on outer surfaces of endoscopes or other similar types of medical delivery devices, either currently existing or later developed, that do not include conductive portions. In addition, at least some of the embodiments of the conductive portion 142, such as the sleeve 460 or the cap 560, may be attached and then removed to and from the outer surface 144 of the endoscope 104 before or after the electrosurgical procedure is performed.

Figure 6:
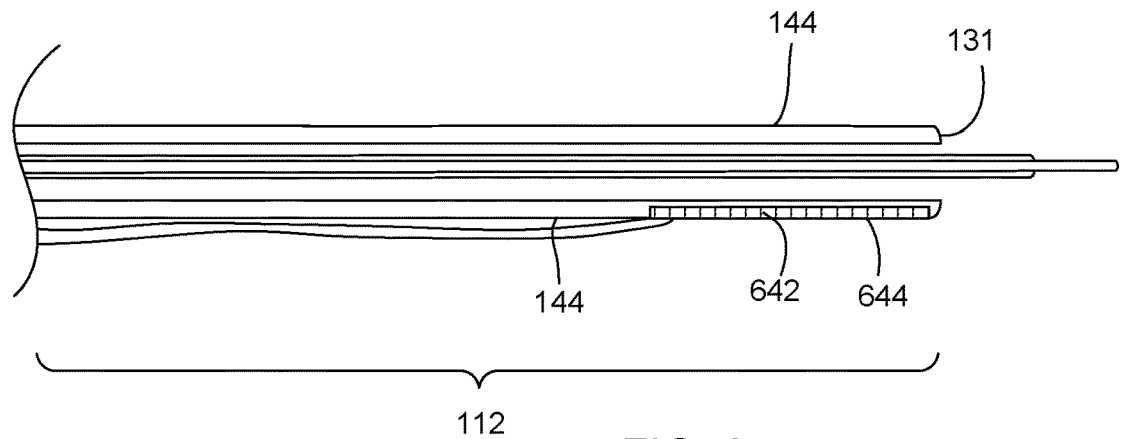
FIG. 6 shows a conductive portion integrated with an outer surface of a medical delivery device.

In alternative example embodiments, instead of being disposed on the outer surface 144 of the outer tubular member 108, a conductive portion 642 may be integral with, part of, or built into the outer surface 144, as shown in FIG. 6. For some configurations, an outer surface 644 of the conductive portion 642 may be flush or even with the outer surface 144 of the tubular member 108. Alternatively, the conductive portion 642 may protrude from the outer surface 144 of the outer tubular member 108.

Figure 7:
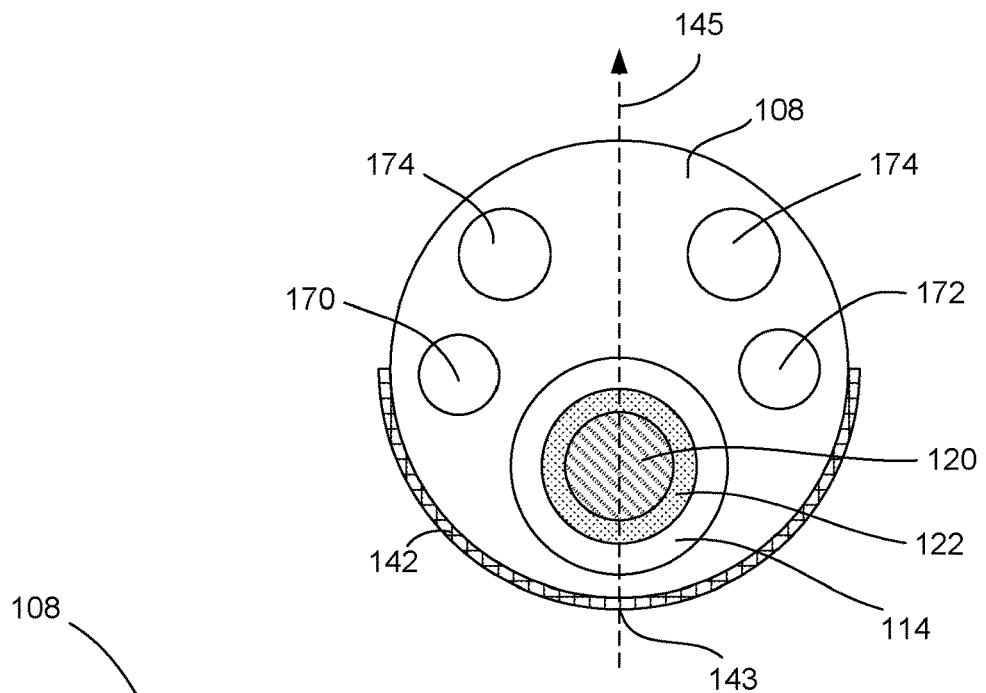
FIG. 7 shows a cross-sectional axial view of the distal portion of the bipolar electrosurgical system shown in FIG. 1, showing a circumferential orientation of a conductive portion.

Although not shown in FIGS. 1-6, the endoscope 104 may include a plurality of lumens or channels, other than the working channel 114, extending within the tubular member 108 from the proximal portion 110 to the distal portion. FIG. 7 shows a cross-sectional view of an example embodiment of the electrosurgical system 102 taken along line 7-7 in FIG. 1. As shown in FIG. 7, in addition to the working channel 114, the endoscope 104 may include an air lumen 170, an irrigation lumen 172, and one or more channels 174 for visualization, such as for illumination or imaging fibers or cables. More lumens or fewer lumens may be included.

Figure 8:
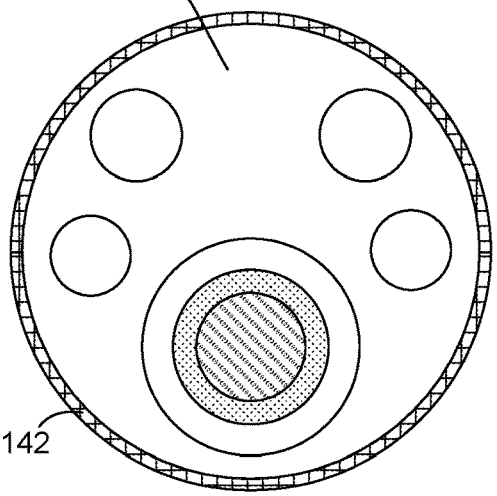
FIG. 8 shows a cross-sectional axial view of the distal portion of the bipolar electrosurgical system shown in FIG. 1, showing an alternative circumferential orientation of the conductive portion.

The conductive portion 142 may be circumferentially disposed at least partially around the outer surface 144 of the tubular member 102. For example, as shown in FIG. 7, the conductive portion 142 may be disposed about 180 degrees around the outer surface 144. Alternatively, the conductive portion 142 may be disposed less than or greater than 180-degrees. For example, as shown in FIG. 8, the conductive portion 142 may be circumferentially disposed completely (i.e., 360-degrees) around the outer surface 144. The circumferential disposition may depend on a surface area to achieve a desired current density ratio between the active member 120 and the conductive portion 142, which may be at least three-to-one, as described above. The surface area may be determined by the length and circumferential width of the conductive portion 142.

Figure 9:
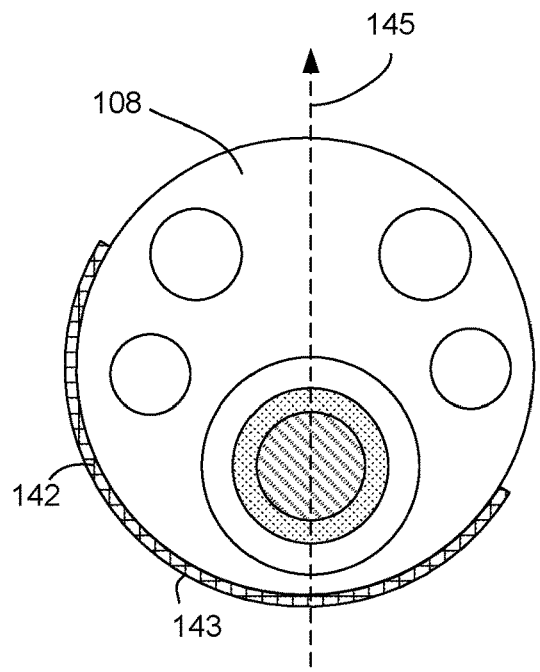
FIG. 9 shows a cross-sectional axial view of the distal portion of the bipolar electrosurgical system shown in FIG. 1, showing another alternative circumferential orientation of the conductive portion.

In general, the conductive portion 142 may have a circumferential disposition that is most likely to make contact with the tissue at the treatment site, which may vary depending on the electrosurgical procedure and/or the area of the body. In some example configurations, the circumferential disposition may be determined relative to a direction in which the electrosurgical device, including the active member 120 and/or the inner tubular member 122, protrudes or radially extends from the outer tubular member 108. For example, as shown in FIG. 7, a central position 143 of the conductive portion 142 may be aligned or substantially aligned with a radial direction in which the ends 126, 128 of the active and inner tubular member 120, 122 extend out of the opening 130 (FIG. 1), as identified by the dotted line 145. Alternatively, as shown in FIG. 9, a central position 143 may be offset by a predetermined number of degrees from a radial direction in which the ends 126, 128 extend.

Figure 10:
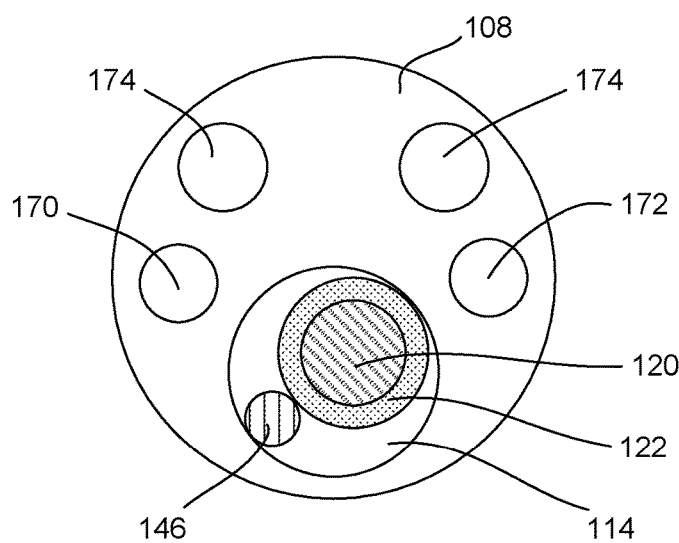
FIG. 10 shows a cross-sectional axial view of the distal portion of the bipolar electrosurgical system shown in FIG. 1, showing a return wire disposed within a tubular member of a medical delivery device.
Figure 11:
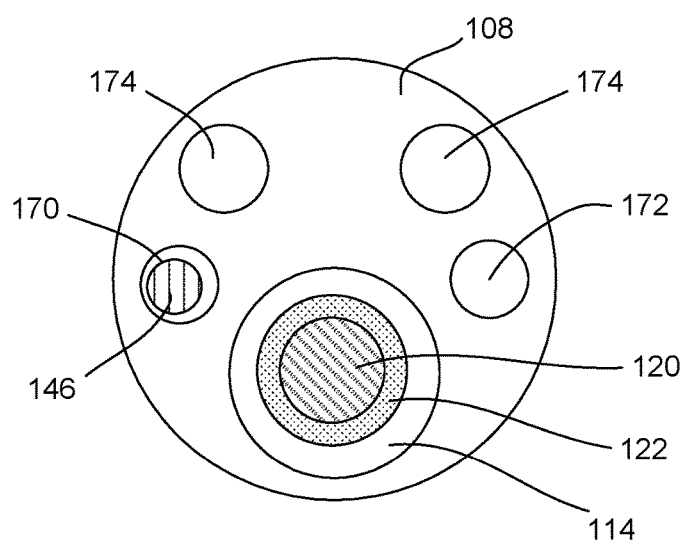
FIG. 11 shows a cross-sectional axial view of the distal portion of the bipolar electrosurgical system shown in FIG. 1, showing an alternative configuration of the return wire disposed within the tubular member of the medical delivery device.
Figure 12:
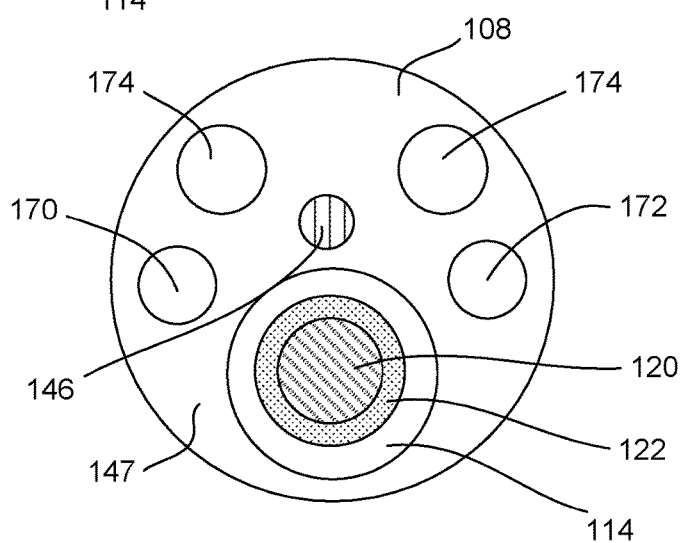
FIG. 12 shows a cross-sectional axial view of the distal portion of the bipolar electrosurgical system shown in FIG. 1, showing another alternative configuration of the return wire disposed within a tubular member of a medical delivery device.

FIG. 10 shows an axial cross-sectional view of an example embodiment of the electrosurgical system 102 taken along line 10-10 in FIG. 1. The cross-sectional view shown in FIG. 10 may be representative of the axial cross-section of the outer tubular member 108 proximal the conductive portion 142. FIG. 10 shows both the return wire 146 and the electrosurgical device 106 (i.e., the active member 120 and the inner tubular member 122) disposed in the working channel 114. In an alternative example configuration of the electrosurgical system 102 shown in FIGS. 1 and 10, the return wire 146 may be disposed within the tubular member in a different portion or area than the working channel 114. For example, as shown in FIG. 11, the return wire 146 may be disposed in the air lumen 170 or the irrigation lumen 172. Alternatively, as shown in FIG. 12, the return 146 wire may be embedded within the body 147 of the outer tubular member 108.

Figure 13:
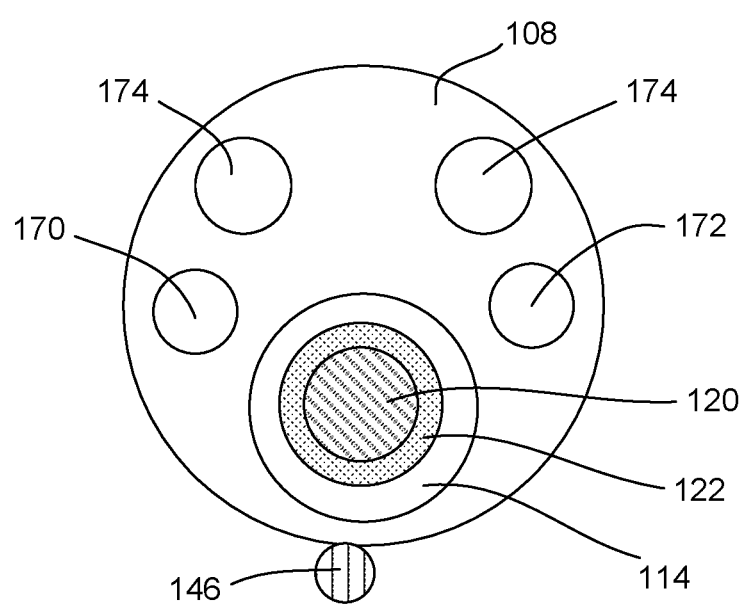
FIG. 13 shows a cross-sectional axial view of the distal portion of the bipolar electrosurgical system shown in FIG. 3, showing a return wire disposed outside of a tubular member of a medical delivery device.

FIG. 13 shows a cross-sectional view of an example embodiment of the electrosurgical system 302 taken along line 13-13 in FIG. 3. The cross-sectional view shown in FIG. 13 may be representative of the cross-section of the outer tubular member 108 proximal the conductive portion 142. As shown in FIG. 13, the return wire 346 may be disposed external to or outside of the outer tubular member 108.

Figure 14:
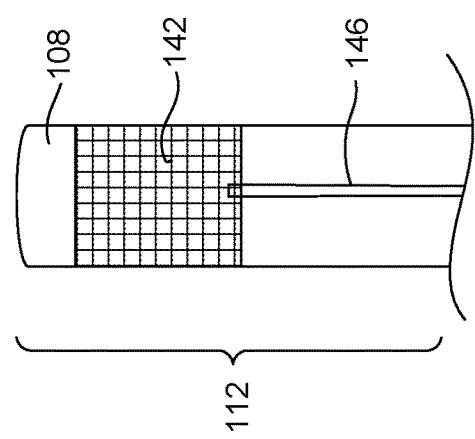
FIG. 14. shows a side view of the distal portion of the bipolar electrosurgical system of FIG. 1, 2 or 3, where the return path is a single return path.

In some example embodiments, the return path may include a single return path. For these example embodiments, the conductive portion may include a single, continuous portion electrically coupled to a single return wire. FIG. 14 shows a side view of an example embodiment of the distal portion 112, such as the distal portion 112 shown in FIG. 3, from an angle showing most if not all of the conductive portion 142 coupled to a single return wire 346.

In alternative example embodiments, the return path may include multiple return paths, such as two return paths. The two return paths may be electrically isolated or substantially electrically isolated from each other. Two return paths may be included to provide a safety feature for use with the power source 132, which may be configured to prevent output of the electrical current unless each of the return paths are in contact with the tissue.

FIGS. 14 shows a side view of an example embodiment of the distal portion 112 shown in FIG. 3 from an angle showing most if not all of the conductive portion 142, where the return path includes a dual return path. To form the dual return path, the conductive portion 142 may include two sub-portions or strips, including a first sub-portion 1442a and a second sub-portion 1442b. The first sub-portion 1442a and the second sub-portion 1442b may be electrically isolated from each other. A gap or spacing 1460 in between the first and second sub-portions 1442a, 1442b may electrically isolate the first and second sub-portions 1442a, 1442b from each other. As shown in FIG. 14, the first and second sub-portions 1442a, 1442b may each be electrically coupled to a respective return wire 1446a, 1446b. The two return wires 1446a, 1446b may each extend proximally external to and alongside the tubular member 108 to the proximal portion 110. Alternatively, one or more both of the return wires 1446a, 1446b may extend to within the tubular member 108, as described above with reference to FIG. 1.

Figure 17:
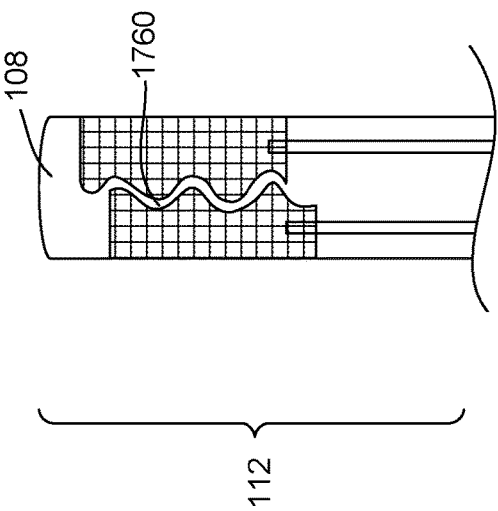
FIG. 17. shows a side view of a third alternative embodiment of the distal portion of the bipolar electrosurgical system of FIG. 1, 2, or 3, where the return path includes two return paths and where the gap has a sinusoidal pattern.
Figure 16:
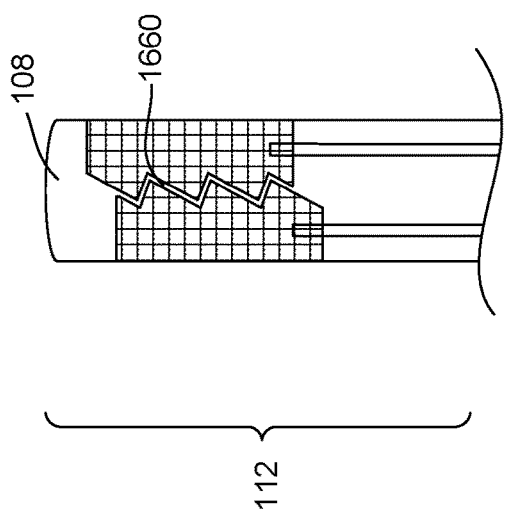
FIG. 16. shows a side view of a second alternative embodiment of the distal portion of the bipolar electrosurgical system of FIG. 1, 2, or 3, where the return path includes two return paths and where the gap has a zig-zag pattern.
Figure 15:
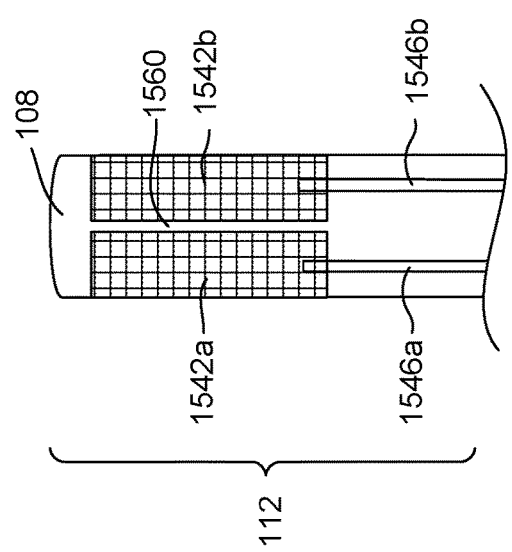
FIG. 15. shows a side view of an alternative embodiment of the distal portion of the bipolar electrosurgical system of FIG. 1, 2 or 3, where the return path includes two return paths and where a gap separating two conductive portions extends in a substantially straight direction.

In one example configuration, as shown in FIG. 15, the gap 1560 separating and electrically isolating the first and second sub-portions 1542a, 1742b may longitudinally extend along the outer surface of the distal portion 112 in a straight or substantially straight direction. In alternative configurations, the gap may longitudinally extend in a non-straight manner. For example, as shown in FIG. 16, a gap 1660 may have a zig-zag pattern. As another example, referring to FIG. 17, the gap 1760 may have a sinusoidal pattern. Various other patterns may be used for the gap, such as helical or spiral, as examples. Alternatively, the gap may not necessarily have a pattern, but may extend in a generally non-straight manner along the outer surface 144 of the distal portion 144. Configuring the gap to extend in a non-straight manner or have a non-straight pattern may be advantageous over configurations where the gap extends straightly in that the non-straight configurations may facilitate contact for both the first and second sub-portions of the conductive portion with the surrounding tissue.

Figure 18:
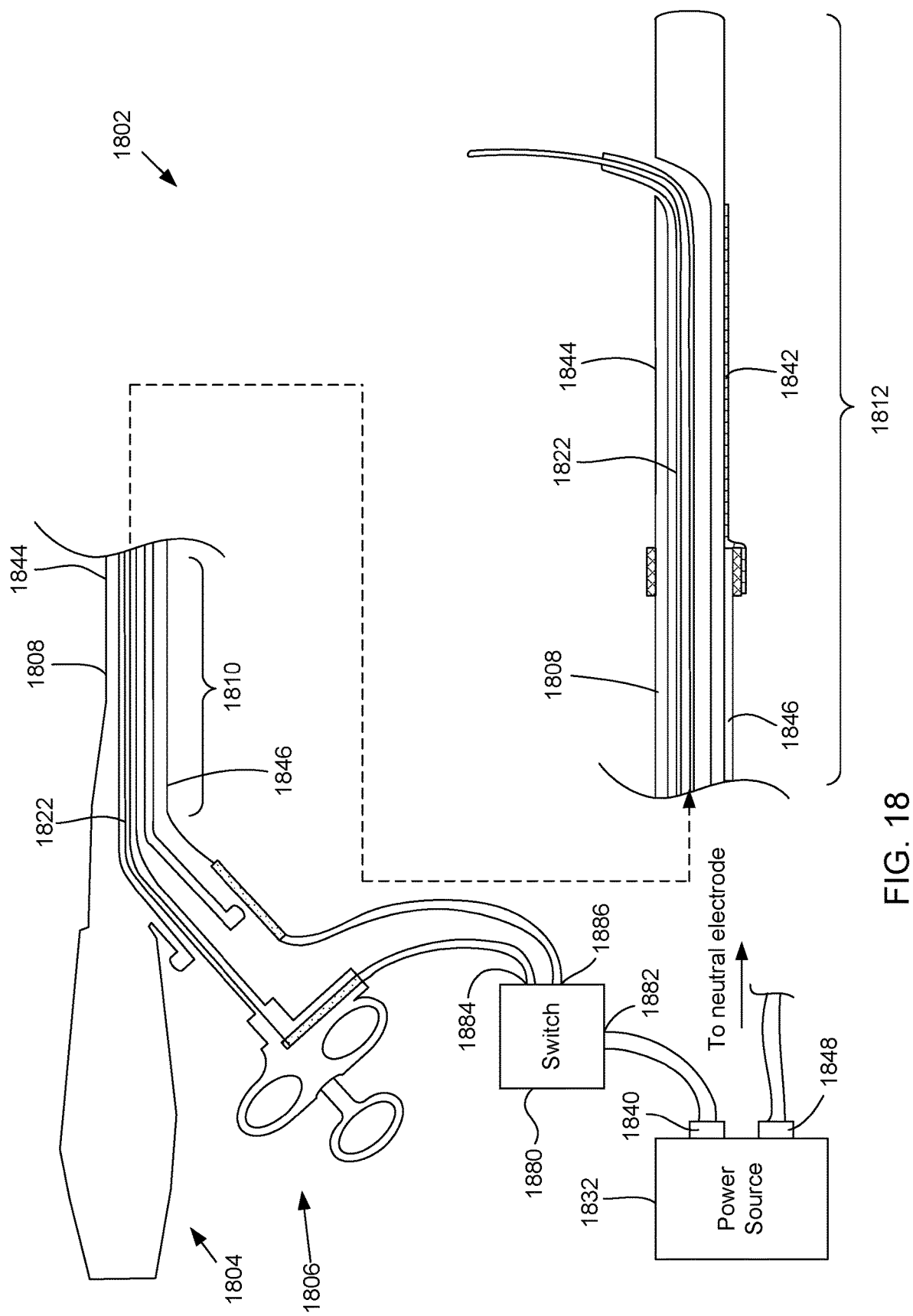
FIG. 18 shows a cross-sectional side view of a medical system that is configured to perform two electrosurgical procedures using monopolar configurations.

FIG. 18 shows an alternative example embodiment of an electrosurgical system 1802 that may include an endoscope 1804 and an electrosurgical device 1806. The electrosurgical system 1802 may be configured to perform two electrosurgical procedures both using a monopolar configuration. A first electrosurgical procedure may be performed with an active member 1820 of the electrosurgical device 1806, and a second electrosurgical procedure may be performed with a conductive portion 1842 disposed or integrated with an outer surface 1844 of an outer tubular member 1808 of the endoscope 1804. An example first procedure may be a cut procedure and an example second procedure may be a coagulation procedure, although other procedures may be used. For the example configuration shown in FIG. 18, the active member 1820 and the conductive portion 1842 may be alternatingly part of the active path.

The electrosurgical system 1802 may include or use a switch 1880 that alternatingly connects an active port 1840 of a power source 1832 with either the active member 1822 or the conductive portion 1842. As shown in FIG. 18, the switch 1880 may include an input 1882 that is electrically coupled to the active port 1840. That switch 1880 may also include a first output 1884 that is electrically coupled to a proximal end of the active member 1822 and a second output 1886 that is electrically coupled to a proximal end of a wire 1846. A return port 1848 may be electrically coupled to a neutral electrode (now shown) for a monopolar configuration.

To perform the first electrosurgical procedure, the switch 1880 may be positioned in a first state or position so that the active port 1840 is electrically coupled to the active member 1822, and the conductive portion 1842 is electrically disconnected from the active port 1840. The power source 1832 may be activated, which may supply electrical current to the active member 1822 to perform the first electrosurgical procedure. For the monopolar configuration, the current may flow to the neutral electrode and back to the return port 1848 of the power source 1832.

To perform the second electrosurgical procedure, the switch 1880 may be positioned in a second state or position so that the active port 1840 is electrically coupled to the conductive portion 1832 of the outer surface 1844 of the endoscope 1804, and the active member 1822 is electrically disconnected from the active port 1840. In some situations, the distal portion 1812 may be repositioned so that the conductive portion 1842 may contact the tissue to perform the second electrosurgical procedure. The power source 1832 may be activated, which may supply electrical current through the wire 1846 to the conductive portion 1842 to perform the second electrosurgical procedure. For the monopolar configuration, the current may flow to the neutral electrode and back to the return port 1848 of the power source 1832.

Figure 19:
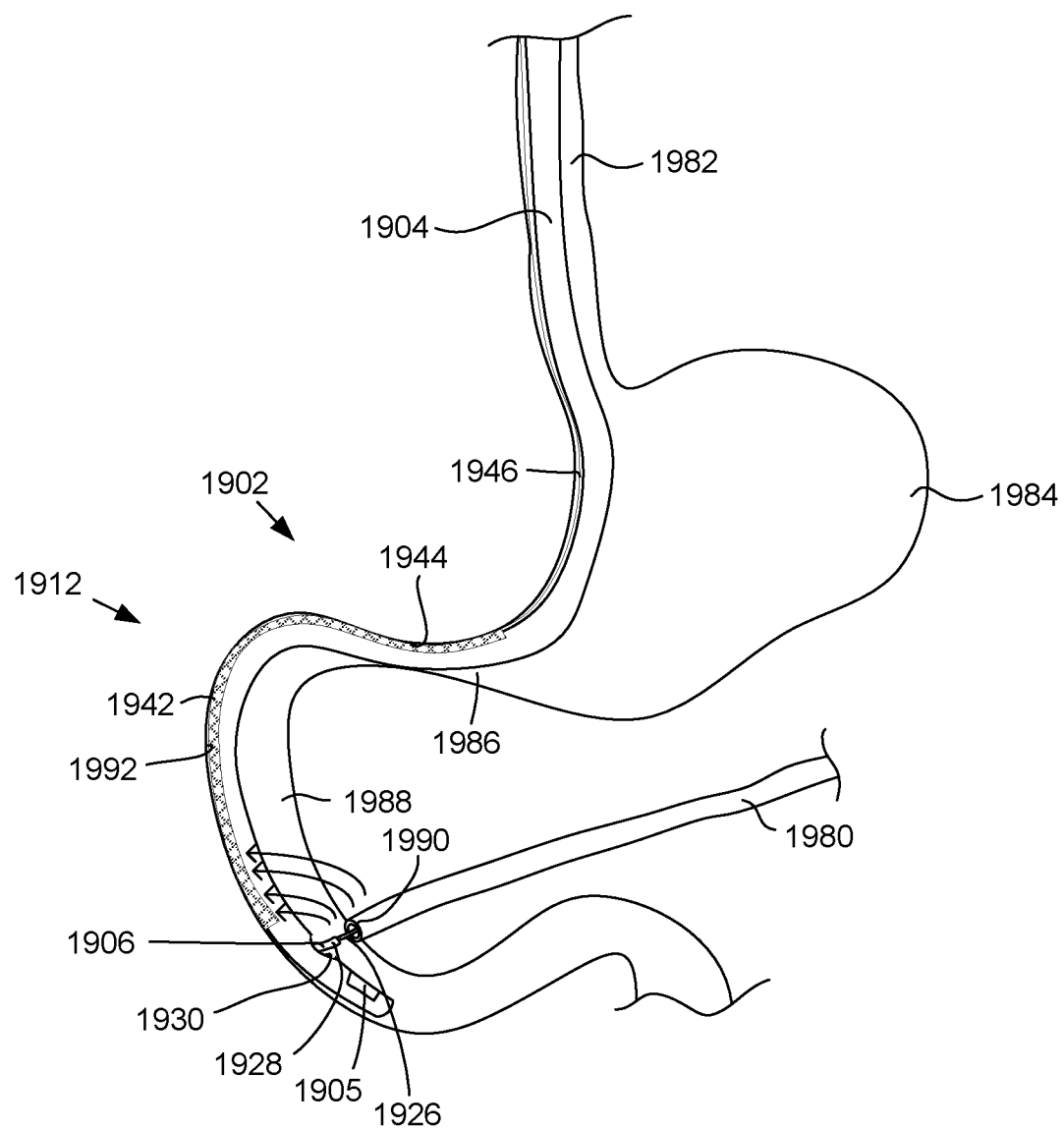
FIG. 19 shows a treatment site within a patient and an electrosurgical system at the treatment site to perform an electrosurgical procedure.

The present description also describes a method of operation of a bipolar electrosurgical system to perform an electrosurgical procedure at a treatment site within a patient. Reference is made to FIG. 19, which shows an example bipolar electrosurgical system 1902 performing a sphincterotomy to access a bile duct 1980, although similar operation may be performed for other electrosurgical procedures at other areas within the patient. The bipolar electrosurgical system 1902 may include a side viewing endoscope 1904 and an electrosurgical device 1906 configured to perform a sphincterotomy and/or cut a sphincter muscle. The electrosurgical device 1906 may be a monopolar device. In the example embodiment shown in FIG. 19, the electrosurgical device 1906 is an endoscopic needle knife that includes a catheter and a cutting wire disposed within the catheter. However, the electrosurgical device 1906 may be a sphincterotome in alternative embodiments.

To perform the sphincterotomy, the endoscope 1904 may be inserted into the patient, through the esophagus 1982 into the stomach 1984. The endoscope 1904 may further be distally moved through the pylorus 1988 into the duodenum 1988, where a distal portion 1912 may be positioned to access the bile duct 1980. The side viewing endoscope 1904 may include an opening 1930, which may be positioned to face a papillae 1990, which provides an opening to the bile duct 1980. The endoscope 1904 may include a visualization and/or camera system 1905 to provide or enable visualization of the treatment site.

The endoscope 1904 may include a conductive portion 1942 disposed on or integrated with an outer surface 1944 of the endoscope 1904. The distal portion 1912 of the endoscope 1904 may be positioned so that the conductive portion 1942 contacts an inner wall 1992 of the duodenum 1988.

As shown in FIG. 19, for some example configurations of the endoscope 1904, the conductive portion 1942 may have a length that is sufficient to proximally extend in the duodenum 1988 and up to and/or past the pylorus 1986 into the stomach 1984 when the endoscope 1904 is in position to perform the sphincterotomy. The endoscope 1904 may be positioned so that the conductive portion 1942 is also and/or alternatively in contact with an inner wall 1994 of the pylorus 1986. The pylorus may be generally constrictive in nature, and so when the endoscope 1904 is positioned in the duodenum 1988, the pylorus 1986 may squeeze or constrict around the outer surface 1944 of the endoscope 1904. As such, by configuring the conductive portion 1942 to have a sufficient length to proximally extend to and/or past the pylorus 1986 when the endoscope 1904 is in position for the sphincterotomy to be performed, even if the conductive portion 1942 does not sufficiently contact the inner wall 1992 of the duodenum 1988, sufficient contact between the conduct portion 1942 and the overall tissue may be ensured or an increased likelihood of the contact may exist because of the likelihood of contact between the conductive portion 1942 and the inner wall 1994 of the pylorus 1986 due to the constrictive nature of the pylorus 1986.

In addition, as shown in FIG. 19, a return wire 1946 may be electrically coupled to the conductive portion 1942. In the example embodiment shown in FIG. 19, the return wire 1946 may extend external to and alongside the endoscope 1904, similar to the configuration shown in FIG. 3. Alternatively, the return wire 1946 may extend to within the endoscope 1904.

When the endoscope 1904 is in position within the duodenum 1988, the endoscopic needle knife 1906 may be distally advanced within a working channel of the endoscope 1904 (as shown in FIGS. 1-13). The endoscopic needle knife 1906 may be distally advanced through the distal portion 1912 to the opening 1930 of the endoscope 1904. Distal ends 1926, 1928 of the cutting wire and catheter, respectively, may be advanced through the opening 1930 until they are exposed outside of the endoscope 1904 near the papillae 1990. The distal end 1926 of the cutting wire may be distally advanced relative to the distal end 1928 of the catheter until it contacts the papillae 1990.

The cutting wire may be electrically coupled to an active port of a power source, such as an ESU unit (see FIGS. 1 and 3), and the conductive portion 1942 and the return wire 1946 may be electrically coupled to a return port of the power source. The power source may be activated, which may send electrical current to the distal end 1926 of the cutting wire to cut the papillae 1990. After passing through the papillae 1990, the electrical current may flow or be drawn to the conductive portion 1942, as denoted by the arrows, and then through the return wire 1946 back to the power source to complete the circuit path.

An alternative method may include a combined cut and coagulation procedure. With reference to FIGS. 13 and 19, the electrosurgical system 1902 may be configured in a monopolar configuration, which may use a neutral electrode attached to the patient. The method may include electrically coupling the cutting wire to the active port of the power source, while electrically disconnecting the conductive portion 1942 and the return wire 1946 from the power source. Electrical current may be supplied to the distal end 1926 of the cutting wire to perform the cutting, such as to cut the papillae. In the event of bleeding or excessive bleeding, an operator of the electrosurgical system 1902 may determine to coagulate the bleeding tissue, in which case the method of operation may further include changing or switching a position of a switch (FIG. 13) so that the conductive portion 1942 is electrically coupled to the power source and the cutting wire is electrically disconnected. The endoscope 1904 may be repositioned so that the conductive portion 1942 is contacting the bleeding portion of the tissue. The power source may then be activated at a coagulation setting to perform the coagulation.

The above described electrosurgical procedure is not limited to a sphincterotomy, and the electrosurgical systems described with reference to FIGS. 1-19 may have other similar methods of operation to perform other electrosurgical procedures, where sufficient contact is made between tissue and a conductive portion of an outer surface of an endoscope or other types of medical delivery devices to perform the electrosurgical procedures.

The foregoing description of various embodiments of the invention has been presented for purposes of illustration and description. It is not intended to be exhaustive or to limit the invention to the precise embodiments disclosed. Numerous modifications or variations are possible in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

The invention claimed is:

1. A method comprising:
delivering a distal portion of a medical delivery device to a treatment site within a patient for performance of a sphincterotomy, wherein the medical delivery device comprises an outer surface and a return electrode that is at least one of disposed on or integrated with the outer surface;
contacting the return electrode of the medical delivery device to an inner wall of a duodenum of the patient when the distal portion is at the treatment site;
delivering an electrosurgical device through a working channel of the medical delivery device to the treatment site; and
cutting a papilla of the patient with an active member of the electrosurgical device while drawing electrical current through the active member of the electrosurgical device and the return electrode of the medical delivery device, and while the return electrode of the medical delivery device is contacting the inner wall of the duodenum.

2. The method of claim 1, further comprising:
contacting the return electrode to a pylorus of the patient, wherein cutting the papilla further comprises cutting the papilla while the return electrode is contacting the pylorus.

3. The method of claim 2, further comprising:
contacting the return electrode to a stomach of the patient, wherein cutting the papilla further comprises cutting the papilla while the return electrode is contacting the stomach.

4. The method of claim 1, wherein the medical delivery device comprises an endoscope.

5. The method of claim 4, wherein the endoscope comprises a side viewing endoscope.

6. The method of claim 1, wherein the outer surface comprises an outer surface of a sleeve or a cap that is removably attachable to an elongate tubular member of the medical delivery device, the return electrode disposed on at least one of the outer surface of the sleeve or the cap.

7. The method of claim 1, wherein the active member comprises a needle knife.

8. The method of claim 1, further comprising: positioning an opening of the medical delivery device adjacent to the papilla.

9. The method of claim 8, wherein delivering the electrosurgical device through the working channel to the treatment site comprises delivering a distal portion of the electrosurgical device through the opening of the medical delivery device adjacent to the papilla.

* * * * *